US00PP34981P2

(12) United States Plant Patent
Miller

(10) Patent No.: US PP34,981 P2
(45) Date of Patent: Feb. 14, 2023

(54) ***LEUCADENDRON* PLANT NAMED 'STARTREUSE'**

(50) Latin Name: ***Leucadendron spissifolium* ssp. *spissifolium* x *discolor***
Varietal Denomination: 'STARTREUSE'

(71) Applicant: Luen Miller, Soquel, CA (US)

(72) Inventor: Luen Miller, Soquel, CA (US)

( * ) Notice: Subject to any disclaimer, the term of this patent is extended or adjusted under 35 U.S.C. 154(b) by 0 days.

(21) Appl. No.: 17/734,654

(22) Filed: May 2, 2022

(51) Int. Cl.
*A01H 6/00* (2018.01)
*A01H 5/02* (2018.01)

(52) U.S. Cl.
USPC ..... Plt./226

(58) Field of Classification Search
USPC ..... Plt./226
CPC ..... A01H 6/00; A01H 5/02
See application file for complete search history.

*Primary Examiner* — Keith O. Robinson
(74) *Attorney, Agent, or Firm* — Cassandra Bright

(57) ABSTRACT

A new and distinct *Leucadendron* species cultivar named 'STARTREUSE' is disclosed, characterized by dense, upright, mostly vertical growth. Branches are willowy and supple. Floral bracts are pale chartreuse to ivory in color. Floral cone is composed of brilliant red and yellow-gold male flowers. The new cultivar is a *Leucadendron*, typically suited for ornamental garden use, or as a cut flower.

1 Drawing Sheet

Latin name of the genus and species: *Leucadendron spissifolium* ssp. *spissifolium* x *discolor.*
Variety denomination: 'STARTREUSE'.

BACKGROUND OF THE INVENTION

The new variety is the result of crossings conducted during the Fall of 2010 by the inventor, Luen Miller in Royal Oaks, Calif. Seed was bulk collected from crossing blocks of various unpatented varieties of *Leucodendron spissifolium* ssp. *spissifolium* and *Leucodendron discolor*. The exact parents cannot be identified. The new variety 'STARTREUSE' was selected during the Fall of 2012 at a commercial nursery in Royal Oaks, Calif.

After selecting and isolating the new cultivar, asexual reproduction of the new cultivar 'STARTREUSE' was first performed at a commercial nursery in Royal Oaks, Calif. in March of 2017. Semi-softwood vegetative terminal cuttings were used for propagation. The inventor continued confidential, controlled evaluation and propagation of 'STARTREUSE'. 'STARTREUSE' has since produced multiple generations and has shown that the unique features of this cultivar are stable and reproduced true to type. Typical asexual reproduction of the new variety is by softwood vegetative cuttings.

SUMMARY OF THE INVENTION

The cultivar 'STARTREUSE' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'STARTREUSE.' These characteristics in combination distinguish 'STARTREUSE' as a new and distinct *Leucadendron* cultivar:

1. Dense, upright, mostly vertical growth
2. Bright green to deep green foliage
3. Willowy, supple twigs and branches
4. Brilliant red and yellow-gold male flower clusters
5. Pale chartreuse bracts to ivory bracts

PARENTAL COMPARISON

Exact parents cannot be identified.

COMMERCIAL COMPARISON

Plants of the new cultivar 'STARTREUSE' can be compared to the commercial variety *Leucadendron* 'Little Bit', unpatented. Plants of 'STARTREUSE' are similar to plants of 'Little Bit' in most horticultural characteristics, however, plants of 'STARTREUSE' differ in the following:

1. Plants of 'STARTREUSE' are approximately twice as tall as plants of 'Little Bit'.
2. Plants of 'STARTREUSE' are narrow, somewhat columnar, compared to the broad, spreading plants of 'Little Bit'.
3. Flower bracts of the new variety are both longer and wider than those of 'Little Bit'.
4. The central cone of male flowers is approximately twice as large in 'STARTREUSE' compared to that of 'Little Bit.

Plants of the new cultivar 'STARTREUSE' can be compared to *Leucadendron* 'PomPon', unpatented. The new variety is similar in some horticultural characteristics. However, the plants of 'STARTREUSE' differ in the following:

1. Growth rate of the new variety is much faster
2. Leaves of the new variety are long, skinny and deep to bright green compared to the short, wide and blue-tinged foliage of 'PomPon'.
3. Plant habit of 'STARTREUSE' is dense and vertical compared to the open and spreading habit of 'PomPon'.

4. Floral bracts of 'STARTREUSE' are narrower and pale chartreuse in color compared to the broader and ivory white floral bracts of 'PomPon'.

BRIEF DESCRIPTION OF THE PHOTOGRAPH

The accompanying photograph was taken using conventional techniques and although colors may appear different from actual colors due to light reflectance it is as accurate as possible by conventional photographic techniques. The photograph depicts a flowering plant of 'Startreuse' at approximately 1.5 years, in a 1-gallon pot.

DETAILED BOTANICAL DESCRIPTION

In the following description, color references are made to The Royal Horticultural Society Colour Chart, 2007, except where general terms of ordinary dictionary significance are used. The following observations and measurements describe 'STARTREUSE' plants grown at a commercial nursery in Royal Oaks, Calif., under bright, unshaded conditions. Average day temperatures were approximately 8° C. to 26° C. and the average night temperature was approximately 3° C. to 18° C. No artificial light, photoperiodic treatments or chemical treatments were given to the plants. Measurements and numerical values represent averages of typical plant types.

Botanical classification: *Leucadendron spissifolium* ssp. *spissifolium* x *discolor* 'STARTREUSE'.

Age of the plant described: Approximately 2 years.

Container size of the plant described: 1-gallon commercial container.

PROPAGATION

Propagation method: Terminal cuttings, hardwood or semi-softwood.

Time to develop roots suitable for transplanting: About 6 to 8 weeks at an average temperature around 25° C.

Root description: Woody, not well branched, colored near Brown N199A and Grey-Brown 199A and 199B. Typically shallow rooted.

PLANT

Growth habit: Compact shrub. Irregular globular shape.

Vigor: Low, slow growing.

Height: 65 cm.

Plant spread: 30 cm.

Branching characteristics: Weak to moderate branching, a pinched plant produces 2 to 3 main lateral branches on average.

Stem description:

- *Length*.—Approximately 7 to 10 cm before pinch.
- *Diameter*.—About 1.1 cm.
- *Texture*.—Glabrous. No scales, bark or lenticels observed.
- *Strength*.—Very strong.
- *Color*.—Near RHS Grey-Brown 199B.
- *Shape*.—Round.

Lateral branches:

- *Length of primary lateral branches*.—Average range 30 to 50 cm. Measured until floral bracts begin.
- *Diameter of lateral branches*.—Approximately 4 mm.
- *Approximate quantity of lateral branches*.—5 to 9.
- *Texture*.—Glabrous.
- *Color*.—Mature: Near RHS Grey-Brown 199B. Immature: Near RHS Yellow-Green 145A.
- *Shape*.—New growth has 4 moderate ridges, forming a rounded quadrangle, older lateral branches are round.
- *Internode*.—Average range 5 to 8 cm.

FOLIAGE

Leaf:

- *Arrangement*.—Spiral.
- *Quantity*.—Approximately 24 to 32, per main branch, including sub-branches.
- *Average length*.—3 to 5.5 cm.
- *Average width*.—8 mm.
- *Shape of blade*.—Narrow oblanceolate.
- *Apex*.—Acute.
- *Base*.—Tapered.
- *Margin*.—Entire.
- *Texture of top surface*.—Glabrous.
- *Texture of bottom surface*.—Glabrous.
- *Aspect*.—Flat. Oldest foliage has a slight twist.
- *Color*.—Young foliage upper side: Near RHS Yellow-Green 146A. Very small apical coloration near Greyed-Orange N170A. Young foliage under side: Near RHS Green 137C. Very small apical coloration near Greyed-Orange N170A. Mature foliage upper side: Near RHS Green 137A. Very small apical coloration near Greyed-Orange N170A. Mature foliage under side: Near RHS Green 137A, marginal coloration near Yellow-Green 146A. Very small apical coloration near Greyed-Orange N170A.
- *Venation*.—Type: Pinnate. Venation color upper side: Indistinguishable from foliage coloration. Venation color under side: Indistinguishable from foliage coloration.
- *Petiole*.—No present, sessile.
- *Fragrance*.—Very faint, grassy scent.

FLOWER

Natural flowering season: Winter.

Inflorescence type and habit: Male only flowers. Minute flowers occurring in spiraling rows on conical spikes. Flowers tubular structure of fused petals, outwardly facing. Flower self-cleaning, persisting approximately 8 weeks on the spike.

Inflorescence longevity: Individual flowers and inflorescences remain ornamental for approximately 2 months. After about 8 weeks individual flowers begin to dry and fall off.

Quantity of flowers and buds per inflorescence: 150 to 180.

Inflorescence size:

- *Diameter*.—Approximately 2.0 cm.
- *Height*.—Approximately 2.0 cm.

Individual flowers:

- *Size*.—Diameter: Approximately 2 mm. Length: Approximately 3 to 4 mm.
- *Shape*.—Tubular.

Petals:

- *Petal arrangement*.—Fused, tubular.
- *Size*.—Length: about 0.5 mm. Width: about 0.3 mm.
- *Shape*.—Oblong.
- *Margin*.—Entire.
- *Apex*.—Rounded.
- *Base*.—Fused.

*Petal quantity*.—Indistinguishable, single, minute structure.
*Texture*.—Glabrous.

Flower color, described as a single structure, as there are no distinguishable upper and lower surfaces:
*Apical flowers*.—When opening: Near RHS Yellow-Green 144B flushed Yellow 12A. Mid-Maturity: Near RHS Orange 28A flushed Orange-Red 34A. Fully opened: Near RHS Orange-Red 34A.
*Main inflorescence flowers*.—When opening: Near RHS Yellow-Green 144B flushed Yellow 12A. Mid-Maturity: Near RHS Yellow-Orange 17A. Fully opened: Near RHS Yellow-Orange 17A flushed Orange-Red 34B.

Bud:
*Shape*.—Ovate.
*Length*.—Approximately 0.8 mm.
*Diameter*.—Approximately 0.4 mm.
*Color*.—Apical buds: Near RHS Yellow-Green 151A. Main inflorescence buds: Near RHS Green-Yellow 2B.

Fragrance: Faint grassy scent.

Involucral bracts:
*General description*.—Dried, curled.
*Number*.—Average range 12 to 16.
*Length*.—Approximately 5 to 7 mm.
*Width*.—Approximately 3 mm.
*Shape*.—Deltate when unfurled.
*Texture*.—Glabrous.
*Apex shape*.—Acute.
*Base*.—Truncate.
*Margin*.—Entire.
*Color*.—Near RHS Brown 200B.

Floral bracts:
Description: Leaf like, occurring just below inflorescence.
*Quantity*.—Average 12 to 15.
*Arrangement*.—Spiral.
*Average length*.—3.5 cm to 5 cm.
*Average width*.—5 to 7 mm.
*Shape of blade*.—Oblanceolate.
*Apex*.—Acute.
*Base*.—Truncate.
*Margin*.—Entire.
*Texture of top surface*.—Glabrous.
*Texture of bottom surface*.—Glabrous.
*Pubescence*.—None.
*Aspect*.—Slight downward fold at midrib.
*Angle of attachment*.—15° to 45°.
*Color*.—Immature: Upper surface: Near Yellow 4D. Under surface: Near Yellow 4D. Mature: Upper surface: Near Yellow 4D. Occasional light stippling near Yellow-Green 144C. Under surface: Near Yellow 4D. Occasional light stippling near Yellow-Green 144C.

Peduncle: Beginning from the lateral branch to lowermost floral bract.
*Length*.—Approximately 2 cm to 4 cm.
*Diameter*.—Approximately 5 mm.
*Texture*.—Glabrous.
*Color*.—Near Green 145C. Frequently streaked near Yellow-Green 154D.

REPRODUCTIVE ORGANS

Minute flowers with compressed productive organs. Reproductive organs not visible under a dissecting microscope. Abundant pollen colored near Yellow 13A.

OTHER CHARACTERISTICS

Seeds and fruits: No seeds/fruits observed.

Disease/pest resistance: Neither other resistance nor susceptibility to normal pests and diseases of *Leucadendron* has been observed.

Temperature tolerance: USDA Zone 9.

What is claimed is:

1. A new and distinct cultivar of *Leucadendron* plant named 'STARTREUSE' as herein illustrated and described.

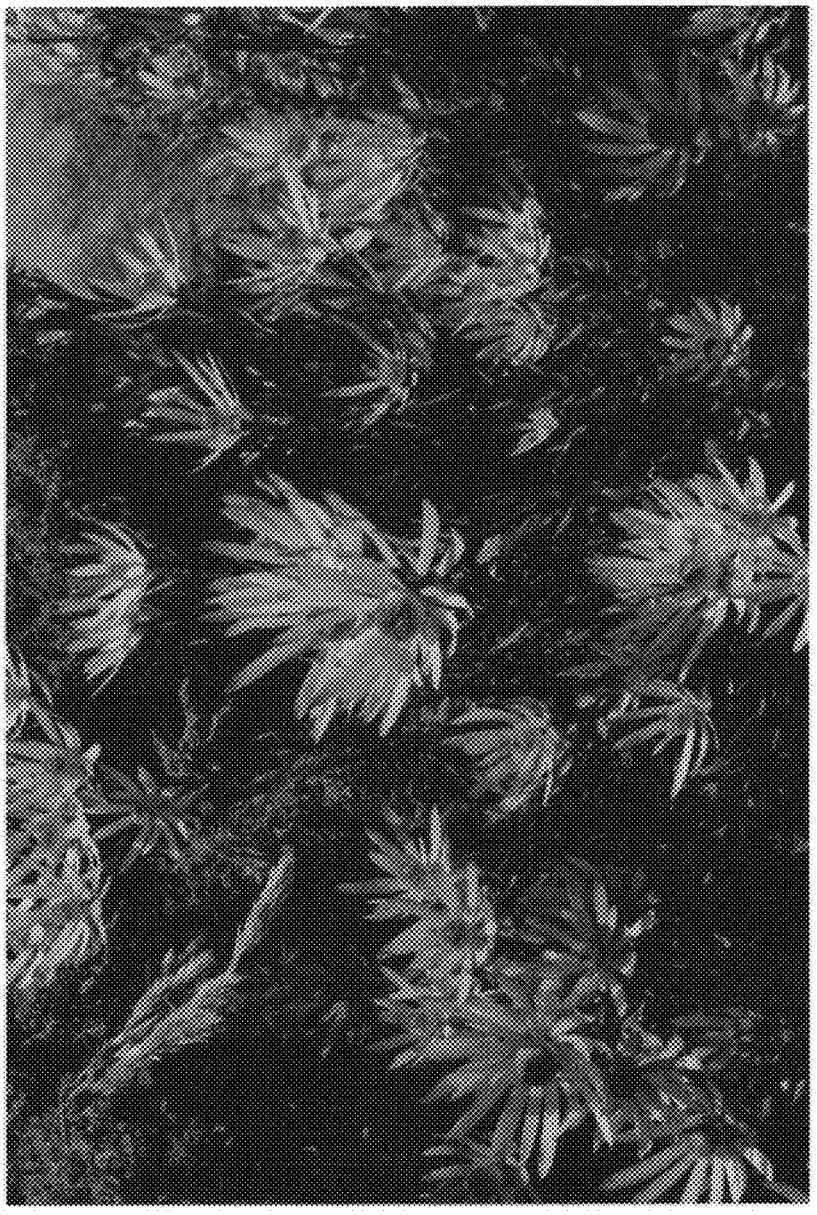

* * * * *